(12) United States Patent
Cilurzo et al.

(10) Patent No.: US 10,426,725 B2
(45) Date of Patent: Oct. 1, 2019

(54) SELF-SUPPORTING FILMS FOR PHARMACEUTICAL AND FOOD USE

(71) Applicant: PHARMAFILM S.R.L., Gaggiano (IT)

(72) Inventors: Francesco Cilurzo, Milan (IT); Paola Minghetti, Monza (IT); Luisa Montanari, Pavia (IT)

(73) Assignee: PHARMAFILM S.R.L., Gaggiano (IT)

( * ) Notice: Subject to any disclaimer, the term of this patent is extended or adjusted under 35 U.S.C. 154(b) by 20 days.

(21) Appl. No.: 15/218,744

(22) Filed: Jul. 25, 2016

(65) Prior Publication Data
US 2017/0035692 A1 Feb. 9, 2017

Related U.S. Application Data

(63) Continuation of application No. 10/577,408, filed as application No. PCT/EP2004/052672 on Oct. 27, 2004, now abandoned.

(30) Foreign Application Priority Data
Oct. 26, 2004 (IT) .............................. MI2003A2087

(51) Int. Cl.
| | |
|---|---|
| A61K 9/00 | (2006.01) |
| A61K 47/10 | (2017.01) |
| A61K 31/375 | (2006.01) |
| A61K 31/5415 | (2006.01) |
| A61K 31/192 | (2006.01) |
| A61K 31/196 | (2006.01) |
| A61K 31/135 | (2006.01) |
| A61K 31/485 | (2006.01) |
| A61K 31/4422 | (2006.01) |
| A61K 31/5513 | (2006.01) |
| A61K 31/5517 | (2006.01) |
| A61K 31/437 | (2006.01) |
| A61K 31/137 | (2006.01) |
| A61K 31/165 | (2006.01) |
| A61K 31/4045 | (2006.01) |
| A61K 31/495 | (2006.01) |
| A61K 47/36 | (2006.01) |
| A23P 30/25 | (2016.01) |
| A23L 29/30 | (2016.01) |
| A23L 33/125 | (2016.01) |
| A23P 20/20 | (2016.01) |

(52) U.S. Cl.
CPC ............ *A61K 9/0056* (2013.01); *A23L 29/35* (2016.08); *A23L 33/125* (2016.08); *A23P 20/20* (2016.08); *A23P 30/25* (2016.08); *A61K 9/006* (2013.01); *A61K 31/135* (2013.01); *A61K 31/137* (2013.01); *A61K 31/165* (2013.01); *A61K 31/192* (2013.01); *A61K 31/196* (2013.01); *A61K 31/375* (2013.01); *A61K 31/4045* (2013.01); *A61K 31/437* (2013.01); *A61K 31/4422* (2013.01); *A61K 31/485* (2013.01); *A61K 31/495* (2013.01); *A61K 31/5415* (2013.01); *A61K 31/5513* (2013.01); *A61K 31/5517* (2013.01); *A61K 47/10* (2013.01); *A61K 47/36* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,222,973 A | 9/1980 | Kasper et al. | |
| 2003/0053962 A1 | 3/2003 | Zerbe et al. | |
| 2003/0054039 A1* | 3/2003 | Zyck ........................ | A61K 8/19 424/488 |
| 2003/0068378 A1* | 4/2003 | Chen .................... | A61K 9/0007 424/486 |
| 2004/0028732 A1 | 2/2004 | Falkenhausen et al. | |
| 2004/0076658 A1 | 4/2004 | Hoess et al. | |
| 2004/0096559 A1* | 5/2004 | Swanson .............. | A23B 7/0205 426/524 |
| 2004/0096569 A1* | 5/2004 | Barkalow ............... | A23L 27/79 426/660 |
| 2004/0228919 A1 | 11/2004 | Houghton et al. | |
| 2004/0253278 A1 | 12/2004 | Maxwell et al. | |
| 2005/0118217 A1 | 6/2005 | Barnhart et al. | |

FOREIGN PATENT DOCUMENTS

| | | |
|---|---|---|
| EP | 0735080 A2 | 10/1996 |
| EP | 1004297 B1 | 1/2006 |
| WO | 2003011259 A1 | 2/2003 |
| WO | WO2004087089 A2 * | 10/2004 |

OTHER PUBLICATIONS

Mahmood Akhtar, Brent S. Murray, Eric Dickinson. Perception of creaminess of model oil-in-water dairy emulsions: Influence of the shear-thinning nature of a viscosity-controlling hydrocolloid. Food Hydrocolloids 20 (2006) 839-847. (Year: 2006).*
U.S. Appl. No. 10/577,480: Patent Board Decision May 26, 2016 (Year: 2016).*
Definition of "self-supporting" from the Free Dictionary, accessed from the Internet on Jun. 26, 2013 from the site: http://www.thefreedictionary.com/self-supporting.
Levitt et al., "Ondansetron compared to dexamethasone and metoclopramide as antiemetics in the chemotherapy of breast cancer with cyclophosphamide, methotrexate and fluorouracil," The New England Journal of Medicine, 1993, 328 (15) pp. 1-9.
Salem S., et al., "Film formation properties of potato starch hydrolysates", Starch/Starke 54, pp. 20-24, (2002).

* cited by examiner

*Primary Examiner* — Michael P Cohen
(74) *Attorney, Agent, or Firm* — Silvia Salvadori, P.C.; Silvia Salvadori

(57) ABSTRACT

Rapidly dissolving self-supporting films for food or pharmaceutical use comprising: a) a filmogenic substance consisting of a maltodextrin; b) a plasticizer; c) an active principle for food or pharmaceutical use, characterized in that said films are free of hydrocolloids.

24 Claims, 3 Drawing Sheets

Figure 1
Table 1 – Formulations used for preparing films by extrusion

| Form. no. | MD DE 40 (g) | MD DE1 (g) | GP (g) | SB (g) | SC (g) | PRX (g) | KP (g) | DS (g) | TR (g) | NF (g) | ZPD (g) | LRZ (g) | BRZ (g) | TRZ (g) | MR (g) | MTC (g) | MEN (g) | A-AC (g) | SLG (g) | ATL (g) | SAL (g) | SMT (g) | CZP (g) | SLG (g) | CTZ (g) | SBT (g) |
|---|---|---|---|---|---|---|---|---|---|---|---|---|---|---|---|---|---|---|---|---|---|---|---|---|---|---|
| 1 | 40 |  | 10 | 3 |  |  |  |  |  |  |  |  |  |  |  |  |  |  |  |  |  |  |  |  |  |  |
| 2 | 40 |  | 7 | 3 |  |  |  |  |  |  |  |  |  |  |  |  |  |  |  |  |  |  |  |  |  |  |
| 3 | 45 |  | 3.5 | 1.5 |  |  |  |  |  |  |  |  |  |  |  |  |  |  |  |  |  |  |  |  |  |  |
| 4 | 40 |  | 3 | 7 |  |  |  |  |  |  |  |  |  |  |  |  |  |  |  |  |  |  |  |  |  |  |
| 5 | 80 |  | 10 | 10 |  |  |  |  |  |  |  |  |  |  |  |  |  |  |  |  |  |  |  |  |  |  |
| 6 | 72 |  | 10 | 10 |  |  |  |  |  |  |  |  |  |  |  |  |  |  |  |  |  |  |  |  |  |  |
| 7 |  | 80 | 10 | 10 | 0.4 |  |  |  |  |  |  |  |  |  |  |  |  |  |  |  |  |  |  |  |  |  |
| 8 |  | 72 | 9 | 9 |  |  |  |  |  |  |  |  |  |  |  |  |  |  |  |  |  |  |  |  |  |  |
| 9 |  | 70 | 9 | 9 |  |  |  |  |  |  |  |  |  |  |  |  |  |  |  |  |  |  |  |  |  |  |
| 10 |  | 62 | 10 | 10 |  | 10 |  |  |  |  |  |  |  |  |  |  |  |  |  |  |  |  |  |  |  |  |
| 11 | 80 |  | 10 | 10 | 0.4 |  | 10 |  |  |  |  |  |  |  |  |  |  |  |  |  |  |  |  |  |  |  |
| 12 |  | 80 | 10 | 10 | 0.4 |  |  | 12 |  |  |  |  |  |  |  |  |  |  |  |  |  |  |  |  |  |  |
| 13 |  | 80 | 10 | 10 | 0.4 |  |  |  | 20 |  |  |  |  |  |  |  |  |  |  |  |  |  |  |  |  |  |
| 14 |  | 80 | 10 | 10 | 0.4 |  |  |  |  | 10 |  |  |  |  |  |  |  |  |  |  |  |  |  |  |  |  |
| 15 | 80 |  | 10 | 10 | 0.4 |  |  |  |  |  | 10 |  |  |  |  |  |  |  |  |  |  |  |  |  |  |  |
| 16 |  | 62 | 10 | 10 |  |  |  |  |  |  |  | 0.5 |  |  |  |  |  |  |  |  |  |  |  |  |  |  |
| 17 | 80 |  | 9 | 9 | 0.2 |  |  |  |  |  |  |  | 0.3 |  |  |  |  |  |  |  |  |  |  |  |  |  |
| 18 |  | 40 | 10 | 10 | 0.4 |  |  |  |  |  |  |  |  | 10 |  |  |  |  |  |  |  |  |  |  |  |  |
| 19 | 75 |  | 3 | 7 |  |  |  |  |  |  |  |  |  |  | 20 |  |  |  |  |  |  |  |  |  |  |  |
| 20 | 58 |  | 9 | 11 | 0.4 |  |  |  |  |  |  |  |  |  |  | 10 |  |  |  |  |  |  |  |  |  |  |
| 21 |  | 62 | 8 | 8 |  |  |  |  |  |  |  |  |  |  |  |  | 0.1 |  |  |  |  |  |  |  |  |  |
| 22 |  | 9 | 10 | 10 | 0.4 |  |  |  |  |  |  |  |  |  |  |  |  | 5 |  |  |  |  |  |  |  |  |
| 23 |  | 80 | 10 | 10 | 0.4 |  |  |  |  |  |  |  |  |  |  |  |  |  | 20 | 25 | 10 | 10 | 10 | 10 | 10 | 10 |

*MTD: maltodextrin; DE: Dextrose equivalents; GP: propylene glycol; SB: sorbitol; SC: colloidal silica; PRX: piroxicam; KP: ketoprofen DS: Sodium diclofenac; TR: Tramadol hydrochloride; MR: Morphine sulfate; NF: Nifedipine; LRZ: Lorazepam; TRZ: Triazolam; BRZ: Bromazepam; ZPD: Zolpidem; MTC: Methoclopramide; MEN: Menthol; A-As: Ascorbic Acid; SLG: Selegiline; ATL: Atenolol; SAL: Salbutamol; SMT: Sumatriptan; CZP: Clozapine; CTZ: Cetirizine

Figure 2

Table 2 – Formulations used for preparing the films

| Form. n. | MD DE 40 (%) | MD DE 11 (%) | GP (%) | SB (%) | MT (%) | TC (%) | Water (%) | Ethanol (%) | SC (%) | GLI (%) | PRX (%) | PRC (%) | DS (%) | NF (%) | CLO (%) | EU (%) | CPT (%) | TIO (%) | DMS (%) | ATEC (%) | DB (%) |
|---|---|---|---|---|---|---|---|---|---|---|---|---|---|---|---|---|---|---|---|---|---|
| 1 | | 25 | 15 | | | | 10 | | | | | | | | | | | | | | |
| 2 | | 70 | 13 | | | | 8 | | | | | | | | | | | | | | |
| 3 | | 31.2 | 5.8 | | 2 | | 13.5 | | | | | | | | | | | | | | |
| 4 | 50 | | | | 18 | | 50 | | | | | | | | | | | | | | |
| 5 | | 70 | 10 | | 2.5 | 8.4 | 28 | 14 | 0.1 | | | 4.8 | | | | | | | | | |
| 6 | | 46.5 | 10 | 5 | 0.4 | | 28 | 7.9 | 0.2 | | | 18 | | | | | | | | | |
| 7 | | 46.5 | 15 | 7.4 | 0.6 | | 19.4 | 12 | 0.2 | | 14 | 13.4 | | | | | | | | | |
| 8 | | 34.4 | 11.2 | 5 | 0.5 | | 26 | 9.7 | 0.2 | | | | 18 | | | | | | | | |
| 9 | | 46.5 | 15 | 3.7 | 0.6 | | 26 | 20 | 0.2 | | | | | 3.6 | | | | | | | |
| 10 | | 46.5 | 15 | 5 | 0.6 | | 26 | 12 | 0.2 | | | | | | 0.8 | | | | | | |
| 11 | | 46.5 | 15 | 5 | 0.6 | | 20 | 12 | | 10 | | | | | | | | | | | |
| 12 | | | 30 | 5 | | | 20 | | | 5 | | | | | | | | | | | |
| 13 | | 50 | 20 | | | | 20 | | 0.2 | | | | | | | 0.1 | | | | | |
| 14 | | 50 | 20 | 5 | 0.6 | | 20 | 12 | 0.2 | | | | | | | | 18 | | | | |
| 15 | | 46.5 | 15 | 5 | 0.6 | | 26 | 12 | 0.2 | | | | | | | | | 18 | | | |
| 16 | | 46.5 | 15 | 7.4 | 0.4 | | 28 | 7.9 | 0.1 | | | | | | | | | | 0.5 | | |
| 17 | | 46.5 | 10 | 6 | 0.6 | | 26 | 12 | 0.2 | | | 4.8 | | | | | | | | | |
| 18 | | 46.5 | 15 | 5 | 0.6 | | 26 | 12 | 0.2 | | | | | | | | | | | 10 | |
| 19 | | 46.5 | | 7.4 | 0.4 | | 28 | 7.9 | 0.1 | | | 4.8 | | | | | | | | | 8 |

*MTD: maltodextrin; DE: Dextrose equivalents; GP: propylene glycol; SB: sorbitol; MT: maltitol; TC: Talc PRX: piroxicam; KP: ketoprofen DS: Sodium diclofenac; MR: Morphine sulfate; NF: Nifedipine; CLO: Clonazepam; BRZ: Bromazepam; ZPD: Zolpidem; PRC: Paracetamol; EU: Eucalyptus; SC: sodium citrate; CPT: captopril; TIO: thiocolchicoside; DMS:dexamethasone; ATEC: Acetyltriethyl citrate;DBS: dibutyl sebacate.

SELF-SUPPORTING FILMS FOR PHARMACEUTICAL AND FOOD USE

CROSS REFERENCE TO RELATED APPLICATIONS

This application is a continuation of U.S. application Ser. No. 10/577,408, filed on Apr. 25, 2006, which is a national stage entry of PCT/EP2004/052672 filed Oct. 27, 2004, which claims the benefit of the priority of Italian application MI2003A002087 filed Oct. 26, 2004, all of which are incorporated by reference herein.

FIELD OF THE INVENTION

The present description relates to rapidly dissolving self-supporting films for pharmaceutical or food use

STATE OF THE ART

Self-supporting films for pharmaceutical or food use have been known for some time.

For example compositions based on edible films are already commercially available. Most of these products use pullulan as the filmogenic component. Pullulan is an expensive ingredient and not easily available. Other materials have been used in place of pullulan. These materials comprise modified starches such as maltodextrin and hydrocolloids such as cellulosic materials, as described for example in US20030053962.

However, these films do not present one or more characteristics typical of pullulan such as rapid dissolution, clean mouth feel, clean flavour and ease of manufacture. That these films do not provide a clean mouth sensation is due to the fact that the hydrocolloids tend to gel on contact with saliva.

One solution to the aforesaid drawbacks is proposed in WO03/011259 from which is noted that, to obtain properties equivalent to those of pullulan, it is crucial that maltodextrin, smaller quantities of hydrocolloid and, additionally, an inert filler are present simultaneously in the filmogenic composition. In this prior patent, therefore, the hydrocolloid content is reduced by virtue of introducing an inert filler at a concentration between 1 and 30% into the film composition. According to said document, however, the hydrocolloid content cannot be reduced below 10% in that according to this prior patent, as in the preceding US20030053962, the presence of this component in the filmogenic composition appears essential for achieving rapid disintegration of the film.

TECHNICAL PROBLEM

Therefore the need was felt for a rapidly dissolving edible film, which would not pose the problems of known edible films for pharmaceutical or food use.

SUMMARY OF THE INVENTION

The Applicant has now surprisingly found that self-supporting edible films for food or pharmaceutical use containing maltodextrin as the filmogenic substance can be prepared which dissolve rapidly despite their not containing hydrocolloids. In particular an aspect of the present invention are self-supporting films comprising:
a) a filmogenic substance consisting of a maltodextrin,
b) a plasticiser
c) an active principle for food or pharmaceutical use,
   characterised in that said films are free of hydrocolloids.

In particular, as seen from the tests described below, the self-supporting films of the invention present disintegration times determined in vitro of less than 1 minute, and in vivo actually less than 45 seconds. Moreover, the self-supporting films impart a clean mouth sensation and in addition can be prepared using simple preparation methods, easily achievable with industrial machinery.

In this respect a further aspect of the present invention is directed towards various processes for preparing the self-supporting edible films of the present invention.

For example, one preparation process for the aforesaid self-supporting film comprises in particular the following steps:
i) the maltodextrin, plasticiser and active ingredient for food or therapeutic use are mixed,
ii) the mixture derived from the preceding step is extruded in an extruder.

Another preparation process according to the present invention comprises in particular the following steps:
i) the maltodextrin, plasticiser and active principle for therapeutic or food use are dispersed in a polar solvent,
ii) the mixture obtained in the preceding step is rolled onto silicone paper and then dried,
iii) the silicone paper is removed from the film obtained in the preceding step.

Another preparation process according to the present invention comprises in particular the following steps:
i) the maltodextrin, plasticiser and active ingredient for food or therapeutic use are mixed,
ii) the mixture was granulated, sieved and mixed with an anti sticking agent
iii) the granules were stored at least for 12 h
iv) the granules derived from the preceding steps were extruded in an extruder for obtaining the edible film.

DESCRIPTION OF THE FIGURES

Table 1 in FIG. 1 shows formulations used for preparing the films of the present invention as described in example 1.

Table 2 in FIG. 2 shows formulations used for preparing the films of the present invention as described in example 2.

DETAILED DESCRIPTION OF THE INVENTION

Figure 3:
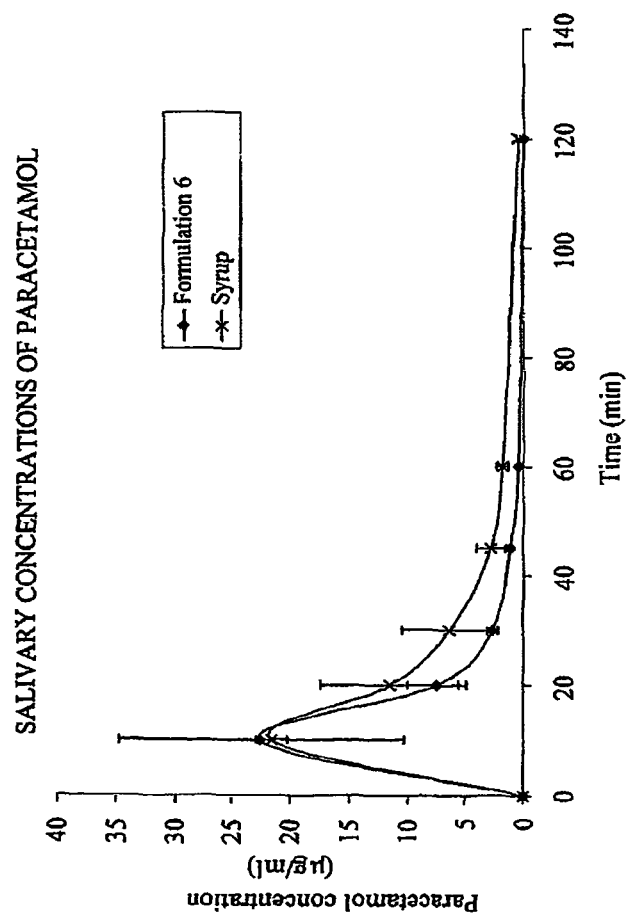
FIG. 3 shows a graph of the in vivo bioavailability of the film of the present Invention prepared as described in example 2 and containing paracetamol (formulation 6 in table 2), and by way of a syrup (Tachipirina syrup), where the y axis shows paracetamol concentration expressed in (μg/ml whereas the x-axis shows time in minutes.

The maltodextrin used in the self-supporting film of the present invention has a dextrose content of less than 50 equivalents, preferably between 11 and 40.

The plasticiser used in the self-supporting films of the present invention is preferably chosen from the group consisting of polyalcohols, citric acid esters, sebacic acid esters or their mixtures. Propylene glycol, glycerine, sorbitol, maltitol or their relative mixtures are particularly preferred.

The active principle for food use is preferably an active principle with a refreshing action on the breath and indicated for oral hygiene, preferably eugenol and menthol or an active principle suitable for nutritional supplementation, preferably mineral salts chosen from those normally used for such purposes or one or more vitamins, the vitamin being ascorbic acid in a particularly preferred embodiment.

The active principle for therapeutic use can be a principle with an essentially topical activity for the oral cavity chosen from antibacterial, antimycotic, antiviral agents or disinfectants of the oral cavity, or can be an active principle with an essentially systemic action chosen from the class consisting of anti-inflammatory, analgesic, antipsychotic, hypnotic, anxiolytic, antihypertensive, myorelaxant, antimigraine, antiparkinsonian, antiemetic, antihistaminic, beta blocking and antiasthmatic agents.

The active principles contained in said films are preferably chosen from the class consisting of: Piroxicam, Ketoprofen, Sodium diclofenac, Tramadol hydrochloride, Morphine, Nifedipine, Diazepam, Lorazepam, Alprazolam, Bromazepam, Triazolam, Lormetazepam, Zolpidem, Paracetamol, Selegiline, Atenolol, Salbutamol, Sumatriptan, Clozapine, Cetirizine, Ondansetron, Fentanyl and their pharmaceutically acceptable salts.

The self-supporting films of the present invention contain maltodextrin in concentrations preferably between 40 and 80% by weight, plasticiser in concentrations between 15 and 55% by weight and active principle for food or pharmaceutical use in quantities between 0.05 and 30% by weight on the total weight of said film, and can possibly contain other excipients chosen from antisticking agents such as microcrystalline cellulose, colloidal silica or talc, sweeteners, flavouring, colouring agents, preservatives, acidity regulating systems or mixtures thereof.

In the process for preparing edible self-supporting films by extrusion, a further aspect of the present invention, the extrusion step (ii) is preferably conducted at a temperature between 60 and 120° C. in a single screw extruder. In the second preparation process, a further aspect of the present invention, the polar solvent used in step (i) is preferably chosen from water, water-miscible solvents or relative mixtures. In accordance with a particularly preferred embodiment the solvent consists of water or a mixture of water and ethanol. The temperature of said step, when a mixture of the aforesaid solvents are used, is preferably between 60 and 105° C.

The self-supporting films of the present invention can be prepared using other methods such as by compacting the filmogenic formulation by the ultrasound technique.

Some examples of formulations for the self-supporting films of the present invention, some processes for preparing said self-supporting films, as well as in vitro and in vivo disintegration tests conducted on films obtained with some of the illustrated formulations are given by way of non limiting examples.

Example 1—Films Prepared by Extrusion Preparation Method

The components of the formulations given in table 1 of FIG. 1 are mixed and extruded with a single screw extruder at a temperature of 105° C.

Disintegration Assay

The test was undertaken in accordance with the method in the European Pharmacopoeia 5.01 Ed., 2.9.1. Disintegration of tablets and capsules (01/2005:20901)

Purified water maintained at 37° C. was used as the medium. The result is the average of 3 determinations±standard deviation.

The results are given in table 3.

TABLE 3

| Form. no. | Disintegration time (in seconds) |
|---|---|
| 2 | 50 ± 4 |
| 5 | 54 ± 4 |
| 6 | 40 ± 1 |
| 8 | 30 ± 1 |
| 11 | 32 ± 2 |
| 17 | 19 ± 1 |

In Vivo Dissolution Assay

Three 4 cm² samples of the formulation under examination were administered to 6 healthy volunteers. The test consists of retaining the film sample in the mouth, and determining the time needed to sense its disappearance.

The test was conducted on formulations no. 2, 5, 17 (table 1).

In each case dissolution time was less than a minute.

Example 2—Films Prepared by Spreading and Evaporation of the Solvent

Preparation Method

The component of the formulations given in table 2 of FIG. 2 are dispersed in the mixture of solvents, given in the same table, and maintained at 80° C. The mixture, maintained at the same temperature, is rolled onto silicon paper and dried.

Disintegration Assay

The test was undertaken in accordance with the method in the European Pharmacopoeia 5.01 Ed., 2.9.1. Disintegration of tablets and capsules (01/2005:20901)

Purified water maintained at 37° C. was used as the medium. The result is the average of 3 determinations±standard deviation.

The results are given in table 4

TABLE 4

| Form. no. | Disintegration time (in seconds) |
|---|---|
| 4 | 27 ± 4 |
| 5 | 36 ± 4 |
| 6 | 50 ± 3 |
| 7 | 37 ± 8 |
| 13 | 32 ± 2 |

In Vivo Dissolution Assay

A 4 cm² sample of the formulation under examination was administered to each of 6 healthy volunteers. The test consists of retaining the film sample in the mouth, and determining the time needed to sense its disappearance.

The test was conducted on formulations no. 3, 6, 13 (table 1).

In each case dissolution time was less than 45 seconds.

Determination of In Vivo Bioavailability

The object of this pilot study was to evaluate the absorption and pharmacokietic profile after a single administration of 50 mg paracetamol carried by Formula 6 (table 2) and by a commercial syrup containing paracetamol (Tachipirina syrup) in 3 healthy volunteers aged between 23 and 24 years. The experiment was conducted as a crossover with a 15 day wash-out period.

With the aim of evaluating the pharmacokinetic profiles of the two formulations, saliva and blood samples were taken before application and at 10 min, 20 min, 45 min, 1 h, 2 h, 3 h, 4 h, 6 h after administration. Paracetamol was determined in the saliva.

The salivary concentrations of paracetamol determined in saliva after administration of the syrup and of the rapidly disintegrating film overlap completely as shown in FIG. 3.

Example 3—Films Prepared by Granulation and Extrusion

Film Composition

| Components | Formulation A (% m/m) | Formulation B (% m/m) | Formulation C (% m/m) | Formulation D (% m/m) |
| --- | --- | --- | --- | --- |
| Maltodextrin (DE 11) | 71 | 47 | 70 | 71.4 |
| Glycerol | 16 | — | 16 | 16.5 |
| Menthol | 1 | — | — | — |
| Microcrystalline cellulose | 12 | 10 | 12 | 12 |
| Paracetamol | — | 21 | — | — |
| Ondansetron | — | — | 2 | — |
| Fentanyl | — | — | — | 0.1 |
| Propylene Glycol | — | 20 | — | — |
| Sodium citrate | — | 2 | — | — |

Preparation Method

The components, with the exception of the microcrystalline cellulose, were mixed into a sigma blade mixer; the time of mixing was 1 hour for formulation B and 30 minutes for formulation A, C and D.

The mixture was transferred in an oscillating granulator and microcrystalline cellulose was added as antisticking agent. The granules are stored for at least 12 hours at ambient temperature and then sieved.

The granules were extruded with a single screw extruder. The extruder temperatures were set in the range 85-130° C.

Disintegration Test

The test was undertaken in accordance with the method in the European Pharmacopoeia 5.01 Ed., 2.9.1. Disintegration of tablets and capsules (01/2005:20901) Purified water maintained at 37° C. was used as the medium. The results were the average of 3 determinations±standard deviation. The disintegration times were less of 45 sec for all the formulations.

In Vivo Dissolution Assay

Three 4 cm$^2$ samples of the formulation A were administered to 6 healthy volunteers. The test consists of retaining the film sample in the mouth, and determining the time needed to sense its disappearance. In each case dissolution time was less than 15 sec.

We claim:

1. A rapidly dissolving self-supporting and edible film, comprising:
    a. between 40 and 80% by weight based on the total weight of said film, of a maltodextrin,
    b. between 15 and 55% by weight based on the total weight of said film, of a plasticizer, and
    c. between 0.05% and 30% by weight based on the total weight of said film, of an active ingredient for food or pharmaceutical use,
    wherein said film is self-supporting, is free from hydrocolloids and has a dissolution time of less than 1 minute.

2. The rapidly dissolving self-supporting and edible film according to claim 1, wherein said in vivo dissolution time is less than 45 seconds.

3. The rapidly dissolving self-supporting and edible film as claim in claim 1, wherein said dissolution time is less than 15 seconds.

4. The rapidly self-supporting and edible film as claimed in claim 1, wherein the maltodextrin (a) has a dextrose content of less than 50 expressed in equivalents.

5. The rapidly self-supporting and edible film as claimed in claim 4, wherein said dextrose content is between 11 and 40.

6. The rapidly self-supporting and edible film as claimed in claim 1, wherein the plasticizer is selected from the group consisting of polyalcohols, citric esters, sebacic acid esters and mixtures thereof.

7. The rapidly dissolving self-supporting and edible film as claimed in claim 1, wherein the plasticizer is selected from the group consisting of propylene glycol, glycerine, sorbitol, maltitol, and mixtures thereof.

8. The rapidly dissolving self-supporting and edible film as claimed in claim 1, wherein the active ingredient has a breath freshening action and/or is indicated for oral hygiene or is an active ingredient suitable for nutritional supplementation.

9. The rapidly dissolving self-supporting and edible film as claimed in claim 8, wherein said active ingredient with a breath freshening action is menthol or eugenol.

10. The rapidly dissolving self-supporting and edible film as claimed in claim 8, wherein said active ingredient for nutritional supplementation is selected from the group consisting of mineral salts, and vitamins.

11. The rapidly dissolving self-supporting and edible film as claimed in claim 10, wherein said vitamin is ascorbic acid.

12. The rapidly dissolving self-supporting and edible film as claimed in claim 1, wherein said active ingredient has essentially topic activity.

13. The rapidly dissolving self-supporting and edible film as claimed in claim 12, wherein said active ingredient is selected from the group consisting of antibacterial agents, antimycotic agents, antiviral agents and disinfectants of the oral cavity.

14. The rapidly dissolving self-supporting and edible film as claimed in claim 1, wherein the active ingredient has systemic activity.

15. The rapidly dissolving self-supporting and edible film as claimed in claim 14, wherein said active ingredient having systemic activity is selected from the group consisting of anti-inflammatory, analgesic, antipsychotic, hypnotic, anxiolytic, antihypertensive, myorelaxant, antimigraine, antiparkinsonian, antiemetic, antihistaminic, betablocking and antiasthmatic agents.

16. The rapidly dissolving self-supporting and edible film as claimed in claim 15, wherein said active ingredient is selected from the group consisting of Piroxicam, Ketoprofen, Diclofenac, Tramadol, Morphine, Nifedipine, Diazepam, Lorazepam, Alprazolam, Bromazepan, Triazolam, Lormetazepam, Zolpiderm, Paracetamol, Selegiline, Atenolol, Salbutamol, Sumatripan, Clozapine, Cetirizine, Ondasetron, Fentanyl, and pharmaceutically acceptable salts thereof.

17. The rapidly dissolving self-supporting and edible film as claimed in claim 1, further comprising other excipients selected from the group consisting of anticaking agents, antisticking agents, sweeteners, flavouring agents, colouring agents, preservatives, acidity regulating systems, and mixtures thereof.

18. A process for preparing the rapidly dissolving self-supporting and edible film as claimed in claim 1, comprising the following steps:
   a. mixing the maltodextrin, plasticizer and active ingredient for food or pharmaceutical use obtaining a mixture thereof; and
   b. extruding the mixture.

19. The process as claimed in claim 18, wherein the extrusion step is carried out at a temperature between 60° C. and 120° C.

20. The process as claimed in claim 18, wherein the extrusion step is conducted in a single screw extruder.

21. A process for preparing the rapidly dissolving self-supporting and edible film as claimed in claim 1, comprising the following steps:
   a. dispersing the maltodextrin, plasticizer and the active ingredient in a polar solvent at a temperature between 60° C. and 105° C., obtaining a mixture thereof;
   b. rolling the mixture obtained in the preceding step onto a silicone paper and drying it to form a film, and
   c. removing the silicone paper from the film obtained.

22. The process as claimed in claim 21, wherein the polar solvent used in step (a) is selected from the group consisting of water, a water miscible solvent, and mixtures thereof.

23. The process as claimed in claim 21, wherein said solvent consists of water or a water-ethanol mixture.

24. The process as claimed in claim 23, wherein the temperature of steps (a) and (b) is between 60° C. and 105° C.

* * * * *